United States Patent
Moeller et al.

(10) Patent No.: US 6,755,872 B1
(45) Date of Patent: Jun. 29, 2004

(54) DYEING AGENT FOR KERATINOUS FIBERS

(75) Inventors: Hinrich Moeller, Monhelm (DE);
Doris Oberkobusch, Duesseldorf (DE);
Horst Hoeffkes, Duesseldorf (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 231 days.

(21) Appl. No.: 10/048,253

(22) PCT Filed: Jul. 31, 2000

(86) PCT No.: PCT/EP00/07405
§ 371 (c)(1),
(2), (4) Date: May 21, 2002

(87) PCT Pub. No.: WO01/10379
PCT Pub. Date: Feb. 15, 2001

(30) Foreign Application Priority Data

Aug. 6, 1999 (DE) ......................................... 199 37 289

(51) Int. Cl.$^7$ ................................................. A61K 7/13
(52) U.S. Cl. ....................... 8/405; 8/406; 8/414; 8/415;
8/570; 8/571; 8/572; 8/574; 8/581; 8/607;
8/608; 548/100; 548/122; 548/215
(58) Field of Search ........................... 8/405, 406, 414,
8/415, 570, 571, 572, 574, 581, 607, 608;
548/100, 122, 215

(56) References Cited
U.S. PATENT DOCUMENTS

| | | | |
|---|---|---|---|
| 4,865,774 A | 9/1989 | Fabry et al. | 252/554 |
| 4,931,218 A | 6/1990 | Schenker et al. | 252/551 |
| 5,294,726 A | 3/1994 | Behler et al. | 554/98 |

FOREIGN PATENT DOCUMENTS

| | | |
|---|---|---|
| DE | 37 23 354 | 1/1989 |
| DE | 37 25 030 | 2/1989 |
| DE | 36 26 344 | 2/1991 |
| DE | 196 49 242 | 4/1998 |
| WO | WO 99/18916 | 4/1999 |
| WO | WO 00/38633 | 7/2000 |
| WO | WO 01/05359 | 1/2001 |

OTHER PUBLICATIONS

The Science of Hair Care, Chapter 7, pp. 235–261, published as vol. 7 of Dermatology, Marcel Dekker Inc. NY/Basle (1986).

The Science of Hair Care, Chapter 8, pp. 263–286, published as vol. 7 of Dermatology, Marcel Dekker, Inc. NY/Basle (1986).

EU Inventory of Cosmetic Ingredients, Colipa, Mar. 1996—on diskette.

*Primary Examiner*—Brian P. Mruk
*Assistant Examiner*—Eisa Elhilo
(74) *Attorney, Agent, or Firm*—Stephen D. Harper; Gregory M. Hill

(57) ABSTRACT

A coloring composition and a method of coloring keratin-containing fibers are provided. The coloring composition contains a mixture of and/or a reaction product of at least one heteroaromatic aldehyde or ketone and at least one aromatic and/or heteroaromatic nitroamine. In the method of the present invention, the heteroaromatic aldehyde or ketone and the nitroamine may be applied to keratin-containing fibers simultaneously or successively.

18 Claims, No Drawings

DYEING AGENT FOR KERATINOUS FIBERS

CROSS REFERENCE TO RELATED APPLICATIONS

This application is a national stage application under 35 U.S.C. § 371 of international application PCT/EP00/07405 filed on Jul. 31, 2000, the international application not being published in English. This application also claims priority under 35 U.S.C. §119 to DE 199 37 289.6 filed on Aug. 6, 1999.

BACKGROUND OF THE INVENTION

This invention relates to a composition for coloring keratin fibers, more particularly human hair, which contains a combination of heteroaromatic aldehydes and ketones and aromatic or heteroaromatic nitroamines, to the use of this combination as a coloring component in hair colorants and to a process for coloring keratin-containing fibers, more particularly human hair.

In general, keratin-containing fibers, for example hair, wool or pelts, are dyed either with substantive dyes or with oxidation dyes which are formed by oxidative coupling of one or more primary intermediates with one another or with one or more secondary intermediates. Primary and secondary intermediates are also known as oxidation dye precursors.

The primary intermediates normally used are primary aromatic amines containing another free or substituted hydroxy or amino group in the para or ortho position, diaminopyridine derivatives, heterocyclic hydrazones, 4-aminopyrazolone derivatives and 2,4,5,6-tetraaminopyrimidine and derivatives thereof.

Special representatives are, for example, p-phenylenediamine, p-toluylenediamine, 2,4,5,6-tetraaminopyrimidine, p-aminophenol, N,N-bis-(2-hydroxyethyl)-p-phenylenediamine, 2-(2,5-diaminophenyl)-ethanol, 2-(2,5-diaminophenoxy)-ethanol, 1-phenyl-3-carboxyamido-4-amino-5-pyrazolone, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine and 2,5,6-triamino-4-hydroxypyrimidine.

The secondary intermediates used are generally m-phenylenediamine derivatives, naphthols, resorcinol and resorcinol derivatives, pyrazolones, m-aminophenols and substituted pyridine derivatives. Particularly suitable secondary intermediates are α-naphthol, 1,5-, 2,7- and 1,7-dihydroxynaphthalene, 5-amino-2-methylphenol, m-aminophenol, resorcinol, resorcinol monomethyl ether, m-phenylenediamine, 2,4-diaminophenoxyethanol, 2-amino-4-(2-hydroxyethylamino)-anisole (Lehmann's blue), 1-phenyl-3-methyl-5-pyrazolone, 2,4-dichloro-3-aminophenol, 1,3-bis-(2,4-diaminophenoxy)-propane, 2-chlororesorcinol, 4-chlororesorcinol, 2-chloro-6-methyl-3-aminophenol, 2-methyl resorcinol, 5-methyl resorcinol, 3-amino-6-methoxy-2-methylaminopyridine and 3,5-diamino-2,6-dimethoxypyridine.

With regard to other typical dye components, reference is specifically made to the series entitled "Dermatology" (Editors: Ch. Culnan and H. Maibach), Marcel Dekker Inc., New York/Basel, 1986, Vol. 7, Ch. Zviak, The Science of Hair Care, Chapter 7 (pages 248–250; Substantive Dyes) and Chapter 8 (pages 264–267; Oxidation Dye Precursors) and to the "Europäische Inventar der Kosmetik-Rohstoffe" published by the European Commission and available on floppy disk from the Bundesverband Deutscher Industrie- und Handelsunternehmen für Arzneimittel, Reformwaren und Körperpflegemittel e.V., Mannheim, Germany.

Although intensive colors with good fastness properties can be obtained with oxidation dyes, the color is generally developed under the influence of oxidizing agents, such as $H_2O_2$ for example, which in some cases can result in damage to the fibers. In addition, some oxidation dye precursors or certain mixtures of oxidation dye precursors can occasionally have a sensitizing effect in people with sensitive skin. Although substantive dyes are applied under more moderate conditions, their disadvantage is that, in many cases, the colors obtained often have inadequate fastness properties.

The use of the combination of heteroaromatic aldehydes and aromatic or heteroaromatic nitroamines for coloring keratin-containing fibers has not hitherto been known.

The problem addressed by the present invention was to provide colorants for keratin fibers, more especially human hair, which would be at least equivalent in quality to conventional oxidation hair dyes in regard to depth of color, grey coverage and fastness properties, but which would not necessarily have to contain oxidizing agents, such as $H_2O_2$ for example. In addition, the colorants according to the invention would have very little, if any, sensitizing potential.

It has surprisingly been found that the combination of the heteroaromatic aldehydes and ketones represented in formula I and aromatic or heteroaromatic nitroamines corresponding to formula II is eminently suitable for coloring keratin-containing fibers, even in the absence of oxidizing agents. They give colors with excellent brilliance and depth of color and lead to a wide variety of shades. In principle, however, oxidizing agents may be present.

SUMMARY OF THE INVENTION

The present invention relates to a composition for coloring keratin-containing fibers, more particularly human hair, containing a combination of heteroaromatic aldehydes corresponding to formula I:

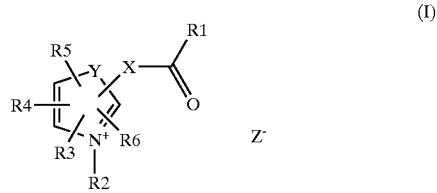

in which
R$^1$ is a hydrogen atom, a $C_{1-4}$ alkyl group, an aryl or heteroaryl group,
R$^2$ is a $C_{1-4}$ alkyl group, an aryl, aralkyl or heteroaryl group,
R$^3$, R$^4$, R$^5$ and R$^6$ represent a hydrogen or halogen atom, a $C_{1-4}$ alkyl, $C_{1-4}$ alkoxy or $C_{1-4}$ hydroxyalkoxy group, a hydroxy, nitro or amino group, which may be substituted by $C_{1-4}$ alkyl groups, or a $C_{1-4}$ acyl group; two of the substituents together may also form a fused aromatic ring or one of the substituents together with R$^1$ or with R$^2$ may form a fused 5-, 6- or 7-membered ring which may also carry a fused aromatic ring,
X is a direct bond, an optionally substituted vinylene, phenylene or vinylenephenylene group,
Y is a sulfur atom, an oxygen atom, the group CR$^7$R$^8$, where R$^7$ and R$^8$ represent a $C_{1-4}$ alkyl group, the group NR$^{10}$, where R$^{10}$ is a C$_{1-4}$ alkyl group, or an optionally substituted vinylene group and Z$^-$ is halide, C$_{1-4}$ alkyl sulfate, arene sulfate, C$_{1-4}$ alkanesulfonate, C$_{1-4}$ perfluoroalkane sulfonate, perhalogenate, sulfate, hydrogen sulfate, tetrafluoroborate, hexafluorophosphate or tetrachlorozincate, and aromatic or heteroaromatic nitroamines corresponding to formula II:

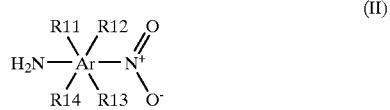

(II)

in which

AR represents benzene, naphthalene, pyridine, quinoline, isoquinoline, pyrimidine, indole, benzimidazole, benzothiazole, indazole, benzoxazole, quinoxaline, quinazoline, cinnoline, acenaphthene, fluorene, biphenyl, diphenylmethane, benzophenone, azobenzene, azonaphthalene, 1-arylazonaphthalene, 2-arylazonaphthalene, diphenylamine, stilbene, benzylidene aminobenzene and R$^{11}$, R$^{12}$, R$^{13}$ and R$^{14}$ represent a hydrogen atom, a halogen atom, a C$_{1-4}$ alkyl, C$_{1-4}$ alkoxy, C$_{1-4}$ aminoalkyl, C$_{1-4}$ hydroxyalkoxy, hydroxy, nitro, carboxy, C$_{1-4}$ alkoxycarbonyl, sulfo, sulfamoyl, arylazo or amino group which may be substituted by C$_{1-4}$ alkyl or C$_{1-4}$ hydroxyalkyl groups, and/or a reaction product of the compounds corresponding to formulae I and II.

DETAILED DESCRIPTION OF THE INVENTION

In the context of the invention, keratin-containing fibers are understood to include wool, pelts, feathers and, in particular, human hair. In principle, however, the colorants according to the invention may also be used to color other natural fibers such as, for example, cotton, jute, sisal, linen or silk, modified natural fibers such as, for example, regenerated cellulose, nitro, alkyl or hydroxyalkyl or acetyl cellulose and synthetic fibers such as, for example, polyamide, polyacrylonitrile, polyurethane and polyester fibers.

Preferred compounds corresponding to formula I are the 4-formyl-1-methylpyridinium, 2-formyl-1-methylpyridinium, 4-formyl-1-ethylpyridinium, 2-formyl-1-ethylpyridinium, 4-formyl-1-benzylpyridinium, 2-formyl-1-benzylpyridinium, 4-formyl-1,2-dimethylpyridinium, 4-formyl-1,3-dimethylpyridinium, 4-formyl-1-methylquinolinium, 2-formyl-1-methylquinolinium, 5-formyl-1-methylquinolinium, 6-formyl-1-methylquinolinium, 7-formyl-1-methylquinolinium, 8-formyl-1-methylquinolinium, 4-acetyl-1-methylpyridinium, 2-acetyl-1-methylpyridinium, 4-acetyl-1-methylquinolinium, 5-acetyl-1-methylquinolinium, 6-acetyl-1-methylquinolinium, 7-acetyl-1-methylquinolinium, 8-acetyl-1-methylquinolinium, 9-formyl-10-methylacridinium, 4-(2-formylvinyl)-1-methylpyridinium, 1,3-dimethyl-2-(4-formylphenyl)-benzimidazolinium, 1,3-dimethyl-2-(4-formylphenyl)-imidazolinium, 2-(4-formylphenyl)-3-methylbenzothiazolium, 2-(4-acetylphenyl)-3-methylbenzothiazolium, 2-(4-formylphenyl)-3-methylbenzoxazolium, 2-(5-formyl-2-furyl)-3-methylbenzothiazolium, 2-(5-formyl-2-furyl)-3-methylbenzothiazolium, 2-(5-formyl-2-thienyl)-3-methylbenzothiazolium, 2-(3-formylphenyl)-3-methylbenzothiazolium, 2-(4-formyl-1-naphthyl)-3-methylbenzothiazolium, 5-chloro-2-(4-formylphenyl)-3-methylbenzothiazolium, 2-(4-formylphenyl)-3,5-dimethylbenzothiazolium, 1-methyl-2-[2-(4-formylphenyl)-ethenyl]-pyridinium, 1-methyl-4-[2-(4-acetylphenyl)-ethenyl]-pyridinium-, 1-benzyl-4-[2-(4-formylphenyl)-ethenyl]-pyridinium-, 1-methyl-4-[2-(4-formylphenyl)-ethenyl]-pyridinium-, 1-methyl-2-[2-(4-formylphenyl)-ethenyl]-pyridinium-, 1-methyl-4-[2-(4-formylphenyl)-ethenyl]-pyridinium-, 1-methyl-4-[2-(4-formylphenyl)-ethenyl]-quinolinium-, 1-methyl-2-[2-(4-formylphenyl)-ethenyl]-quinolinium-, 1-methyl-2-[2-(5-formyl-2-furyl)-ethenyl]-quinolinium-, 1-methyl-2-[2-(5-formyl-2-thienyl)-ethenyl]-quinolinium, 1-methyl-2-[2-(4-formylphenyl) ethenyl]-benzothiazolinium, 1,3-dimethyl-2-[2-(4-formylphenyl)-ethenyl]-benzimidazolinium, 1,3-dimethyl-2-[2-(4-formylphenyl)-ethenyl]-imidazolinium, 1-methyl-5-oxo-indeno[1,2-b]pyridinium, 1-ethyl-5-oxo-indeno[1,2-b] pyridinium, 1-benzyl-5-oxo-indeno[1,2-b]pyridinium, (4-ethyl-4-azonio-9-fluorenone), (4-benzyl-4-azonio-9-fluorenone), 2-methyl-5-oxo-indeno[1,2-c]pyridinium, 2-methyl-9-oxo-indeno[2,1-c]pyridinium, 1-methyl-9-oxo-indeno[2,1-b]pyridinium salts, more particularly the benzenesulfonates, p-toluenesulfonates, methanesulfonates, perchlorates, sulfates, chlorides, bromides, iodides, tetrachlorozincates, methyl sulfates, trifluoromethanesulfonates, hexafluorophosphates, tetrafluroborates and mixtures thereof.

Examples of preferred aromatic or heteroaromatic nitroamines corresponding to formula II include 4-amino-1-nitrobenzene, 2-amino-1-nitrobenzene, 1,4-diamino-2-nitrobenzene, 1,2-diamino-4-nitrobenzene, 1-amino-2-methyl-6-nitrobenzene, 3-amino-6-methylamino-2-nitropyridine, Picramic acid, 1-(2(3)-nitro-4-amino)-phenylazo-2-hydroxy-7-trimethylammonium naphthalene chloride, 1-hydroxy-2-amino-4,6-dinitrobenzene, 1-amino-2-nitro-4-bis-(2-hydroxyethyl)-aminobenzene, 1-amino-2-(2-hydroxyethyl)-amino-5-nitrobenzene (HC Yellow 5), 1-amino-2-nitro-4-(2-hydroxyethyl)-aminobenzene (HC Red 7), 2-chloro-5-nitro-N-hydroxyethyl-1,4-phenylenediamine, 1-(2-hydroxyethyl)-amino-2-nitro-4-aminobenzene (HC Red 3), 4-amino-3-nitrophenol, 4-amino-2-nitrophenol, 6-nitro-o-toluidine, 1-amino-3-methyl-4-(2-hydroxyethyl)-amino-6-nitrobenzene (HC Violet 1), 1-amino-2-nitro-4-(2,3-dihydroxypropyl)-amino-5-chlorobenzene (HC Red 10), 4-amino-2-nitrodiphenylamino-2'-carboxylic acid (2-(4-amino-2-nitroanilino)-benzoic acid), 6-nitro-2,5-diaminopyridine, 2-amino-6-chloro-4-nitrophenol, 2-amino-6-chloro-4-nitrophenol, 1-amino-2-(3-nitrophenylazo)-7-phenylazo-8-naphthol-3,6-disulfonic acid, disodium salt (Acid Blue 29), 1-amino-2-(2-hydroxy-4-nitrophenylazo)-8-naphthol-3,6-disulfonic acid, disodium salt (Palatinchrome Green), 1-amino-2-(3-chloro-2-hydroxy-5-nitrophenylazo)-8-naphthol-3,6-disulfonic acid, disodium salt (Gallion), 4-amino-4'-nitrostilbene-2,2'-disulfonic acid, disodium salt, 2,4-diamino-3',5'-dinitro-2'-hydroxy-5-methylazobenzene (Mordant Brown 4), 4'-amino-4-nitrodiphenylamine-2-sulfonic acid, 4'-amino-3'-nitrobenzophenone-2-carboxylic acid, 1-amino-4-nitro-2-(2-nitrobenzylideneamino)-benzene, 2-[2-(diethylamino)-ethylamino]-5-nitroaniline, 3-amino-4-hydroxy-5-nitrobenzenesulfonic acid, (hydrate), 3-amino-3'-nitrobiphenyl, 3-amino-4-nitroacenaphthene, 2-amino-1-nitronaphthalene, 5-amino-6-nitrobenzo-1,3-dioxol and mixtures of the above.

These compounds are largely known from the literature or are commercially obtainable or may be obtained by known syntheses.

The above-mentioned compounds corresponding to formula I and formula II are used in the compositions according to the invention in quantities of preferably 0.03 to 65 mmol and more preferably 1 to 40 mmol, based on 100 g of the colorant as a whole. They may be used as substantive colorants or in the presence of typical oxidation dye precursors.

Colorants which contain the combination according to the invention as sole coloring component are preferably used for colors in the yellow, orange, red and violet range.

In order to obtain further and more intensive colors, the colorants according to the invention may additionally contain color intensifiers. The color intensifiers are preferably selected from the group consisting of piperidine, piperidine-2-carboxylic acid, piperidine-3-carboxylic acid, piperidine4-carboxylic acid, pyridine, 2-hydroxypyridine, 3-hydroxypyridine, 4-hydroxypyridine, imidazole, 1-methyl imidazole, histidine, pyrrolidine, proline, pyrrolidone, pyrrolidone-5-carboxylic acid, pyrazole, 1,2,4-triazole, piperazidine, derivatives and physiologically compatible salts thereof.

The color intensifiers mentioned above may be used in a quantity of 0.03 to 65 and more particularly 1 to 40 mmol, based on 100 g of the colorant as a whole.

Various combinations of the compounds corresponding to formula I and/or II may also be used together in all colorants. Similarly, various color intensifiers may also be used together.

Oxidizing agents, for example $H_2O_2$, need not be present. However, it may be desirable in some cases to add hydrogen peroxide or other oxidizing agents to the compositions according to the invention to obtain shades which are lighter than the keratin-containing fibers to be colored. Oxidizing agents are generally used in a quantity of 0.01 to 6% by weight, based on the solution applied. A preferred oxidizing agent for human hair is $H_2O_2$.

In one preferred embodiment, the colorants according to the invention contain typical substantive dyes, for example from the group of nitrophenylenediamines, nitroaminophenols, anthraquinones or indophenols, in addition to the compounds present in accordance with the invention in order further to modify the color tones. Examples of suitable substantive dyes are the compounds known under the International names or commercial names of HC Yellow 2, HC Yellow 4, HC Yellow 6, Basic Yellow 57, Disperse Orange 3, HC Red BN, Basic Red 76, HC Blue 2, Disperse Blue 3, Basic Blue 99, Disperse Violet 1, Disperse Violet 4, Disperse Black 9, Basic Brown 16 and Basic Brown 17 and also 2-amino-6-chloro-4-nitrophenol, 6-nitro-1,2,3,4-tetrahydroquinoxaline, 4-N-ethyl-1,4-bis-(2'-hydroxyethylamino)-2-nitrobenzene hydrochloride and 1-methyl-3-nitro-4-(2'-hydroxyethyl)-aminobenzene. The compositions according to the invention in this embodiment contain the substantive dyes in a quantity of, preferably, 0.01 to 20% by weight, based on the colorant as a whole.

In addition, the compositions according to the invention may also contain naturally occurring dyes such as, for example, henna red, henna neutral, henna black, camomile blossom, sandalwood, black tea, black alder bark, sage, logwood, madder root, catechu, sedre and alkanet.

Compounds I and II present in accordance with the invention or the color intensifiers and substantive dyes optionally present do not have to be single compounds. Instead, the hair colorants according to the invention—due to the processes used for producing the individual dyes—may contain small quantities of other components providing they do not adversely affect the coloring result or have to be ruled out for other reasons, for example toxicological reasons.

The colorants according to the invention produce intensive colors even at physiologically compatible temperatures of <45° C. Accordingly, they are particularly suitable for coloring human hair. For application to human hair, the colorants are normally incorporated in a water-containing cosmetic carrier. Suitable water-containing cosmetic carriers are, for example, creams, emulsions, gels or even surfactant-containing foaming solutions, for example shampoos or other formulations suitable for application to the keratin-containing fibers. If necessary, the colorants may even be incorporated in water-free carriers.

The colorants according to the invention may also contain any of the known active substances, additives and auxiliaries typical of such formulations. In many cases, the colorants contain at least one surfactant, both anionic and zwitterionic, ampholytic, nonionic and cationic surfactants being suitable in principle. In many cases, however, it has been found to be of advantage to select the surfactants from anionic, zwitterionic or nonionic surfactants.

Suitable anionic surfactants for the compositions according to the invention are any anionic surface-active substances suitable for use on the human body. Such substances are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether, amide groups and hydroxyl groups may also be present in the molecule. The following are examples of suitable anionic surfactants—in the form of the sodium, potassium and ammonium salts and the mono-, di- and trialkanolammonium salts containing 2 or 3 carbon atoms in the alkanol group:

- linear fatty acids containing 10 to 22 carbon atoms (soaps),
- ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16,
- acyl sarcosides containing 10 to 18 carbon atoms in the acyl group,
- acyl taurides containing 10 to 18 carbon atoms in the acyl group,
- acyl isethionates containing 10 to 18 carbon atoms in the acyl group,
- sulfosuccinic acid mono- and dialkyl esters containing 8 to 18 carbon atoms in the alkyl group and sulfosuccinic acid monoalkyl polyoxyethyl esters containing 8 to 18 carbon atoms in the alkyl group and 1 to 6 oxyethyl groups,
- linear alkane sulfonates containing 12 to 18 carbon atoms,
- linear α-olefin sulfonates containing 12 to 18 carbon atoms,
- α-sulfofatty acid methyl esters of fatty acids containing 12 to 18 carbon atoms,
- alkyl sulfates and alkyl polyglycol ether sulfates corresponding to the formula R—O(CH$_2$—CH$_2$O)$_x$—SO$_3$H, in which R is a preferably linear alkyl group containing 10 to 18 carbon atoms and x=0 or 1 to 12,
- mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of addition products of around 2 to 15 molecules of ethylene oxide and/or propylene oxide with fatty alcohols containing 8 to 22 carbon atoms.

Preferred anionic surfactants are alkyl sulfates, alkyl polyglycol ether sulfates and ether carboxylic acids containing 10 to 18 carbon atoms in the alkyl group and up to 12 glycol ether groups in the molecule and, in particular, salts of saturated and, more particularly, unsaturated $C_{8-22}$ carboxylic acids, such as oleic acid, stearic acid, isostearic acid and palmitic acid.

In the context of the invention, zwitterionic surfactants are surface-active compounds which contain at least one quaternary ammonium group and at least one $-COO^{(-)}$ or $-SO_3^{(-)}$ group in the molecule. Particularly suitable zwitterionic surfactants are the so-called betaines, such as N-alkyl-N,N-dimethyl ammonium glycinates, for example coconutalkyl dimethyl ammonium glycinate, N-acylaminopropyl-N,N-dimethyl ammonium glycinates, for example coconutacylaminopropyl dimethyl ammonium glycinate, and 2-alkyl-3-carboxymethyl-3-hydroxyethyl imidazolines containing 8 to 18 carbon atoms in the alkyl or acyl group and coconutacylaminoethyl hydroxyethyl carboxymethyl glycinate. A preferred zwitterionic surfactant is the fatty acid amide derivative known by the CTFA name of Cocamidopropyl Betaine.

Ampholytic surfactants are surface-active compounds which, in addition to a $C_{8-18}$ alkyl or acyl group, contain at least one free amino group and at least one —COOH or $-SO_3H$ group in the molecule and which are capable of forming inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkyl amidopropyl glycines, N-alkyl taurines, N-alkyl sarcosines, 2-alkyl aminopropionic acids and alkyl aminoacetic acids containing around 8 to 18 carbon atoms in the alkyl group. Particularly preferred ampholytic surfactants are N-coconutalkyl aminopropionate, coconutacyl aminoethyl aminopropionate and $C_{12-18}$ acyl sarcosine.

Nonionic surfactants contain, for example, a polyol group, a polyalkylene glycol ether group or a combination of polyol and polyglycol ether groups as the hydrophilic group. Examples of such compounds are products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group, $C_{12-22}$ fatty acid monoesters and diesters of products of the addition of 1 to 30 moles of ethylene oxide onto glycerol, $C_{8-22}$ alkyl mono- and oligoglycosides and ethoxylated analogs thereof, products of the addition of 5 to 60 moles of ethylene oxide onto castor oil and hydrogenated castor oil, products of the addition of ethylene oxide onto sorbitan fatty acid esters, products of the addition of ethylene oxide onto fatty acid alkanolamides.

Examples of cationic surfactants suitable for use in the hair treatment formulations according to the invention are, in particular, quaternary ammonium compounds. Preferred quaternary ammonium compounds are ammonium halides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Other cationic surfactants suitable for use in accordance with the invention are the quaternized protein hydrolyzates.

Also suitable for use in accordance with the invention are cationic silicone oils such as, for example, the commercially available products Q2-7224 (manufacturer: Dow Corning; a stabilized trimethyl silyl amodimethicone), Dow Corning 929 Emulsion (containing a hydroxylamino-modified silicone which is also known as amodimethicone), SM-2059 (manufacturer: General Electric), SLM-55067 (manufacturer: Wacker) and Abil®-Quat 3270 and 3272 (manufacturer: Th. Goldschmidt; diquaternary polydimethyl siloxanes, quaternium-80).

Alkyl amidoamines, particularly fatty acid amidoamines, such as the stearyl amidopropyl dimethyl amine obtainable as Tego Amid®S 18, are distinguished not only by their favorable conditioning effect, but also and in particular by their ready biodegradability.

Quaternary ester compounds, so-called "esterquats", such as the methyl hydroxyalkyl dialkoyloxyalkyl ammonium methosulfates marketed under the trade name of Stepantex®, are also readily biodegradable.

One example of a quaternary sugar derivative suitable for use as a cationic surfactant is the commercially available product Glucquat®100 (CTFA name: Lauryl Methyl Gluceth-10 Hydroxypropyl Dimonium Chloride).

The compounds containing alkyl groups used as surfactants may be single compounds. In general, however, these compounds are produced from native vegetable or animal raw materials so that mixtures with different alkyl chain lengths dependent upon the particular raw material are obtained.

The surfactants representing addition products of ethylene and/or propylene oxide with fatty alcohols or derivatives of these addition products may be both products with a "normal" homolog distribution and products with a narrow homolog distribution. Products with a "normal" homolog distribution are mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. The use of products with a narrow homolog distribution can be of advantage.

Other active substances, auxiliaries and additives are, for example, nonionic polymers such as, for example, vinyl pyrrolidone\vinyl acrylate copolymers, polyvinyl pyrrolidone and vinyl pyrrolidone/vinyl acetate copolymers and polysiloxanes, cationic polymers, such as quaternized cellulose ethers, polysiloxanes containing quaternary groups, dimethyl diallyl ammonium chloride polymers, acrylamide/dimethyl diallyl ammonium chloride copolymers, dimethyl aminoethyl methacrylate/vinyl pyrrolidone copolymers quaternized with diethyl sulfate, vinyl pyrrolidone/imidazolinium methochloride copolymers and quaternized polyvinyl alcohol, zwitterionic and amphoteric polymers such as, for example, acrylamidopropyl/trimethyl ammonium chloride/acrylate copolymers and octyl acrylamide/methyl methacrylate/tert.butyl aminoethyl methacrylate/2-hydroxypropyl methacrylate copolymers, anionic polymers such as, for example, polyacrylic acids, crosslinked polyacrylic acids, vinyl acetate/crotonic acid copolymers, vinyl pyrrolidone/vinyl acrylate copolymers, vinyl acetate/butyl maleate/isobornyl acrylate copolymers, methyl vinyl ether/maleic anhydride copolymers and acrylic acid/ethyl acrylate/N-tert.butyl acrylamide terpolymers, thickeners, such as agar agar, guar gum, alginates, xanthan gum, gum arabic, karaya gum, locust bean gum, linseed gums, dextrans, cellulose derivatives, for example methyl cellulose, hydroxyalkyl cellulose and carboxymethyl cellulose, starch fractions and derivatives, such as amylose, amylopectin and dextrins, clays such as, for example, bentonite or fully synthetic hydrocolloids such as, for example, polyvinyl alcohol, structurants, such as glucose and maleic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensation products thereof with fatty acids and quaternized protein hydrolyzates, perfume oils, dimethyl isosorbide and cyclodextrins, solubilizers, such as ethanol, isopropanol, ethylene glycol, propylene glycol, glycerol and diethylene glycol, antidandruff agents, such as Piroctone Olamine and Zinc Omadine, other substances for adjusting the pH value, active substances, such as panthenol, pantothenic acid, allantoin, pyrrolidone carboxylic acids and salts thereof, plant extracts and vitamins, cholesterol, UV filters, consistency factors, such as sugar esters, polyol esters or polyol alkyl ethers, fats and waxes, such as spermaceti, beeswax, montan wax, paraffins, fatty alcohols and fatty acid esters, fatty acid alkanolamides, complexing agents, such as EDTA, NTA and phosphonic acids, swelling and penetration agents, such as glycerol, propylene glycol monoethyl ether, carbonates, hydrogen carbonates, guanidines, ureas and primary, secondary and tertiary phosphates, imidazoles, tannins, pyrrole, opacifiers, such as latex, pearlizers, such as ethylene glycol mono- and distearate, propellents, such as propane/butane mixtures, $N_2O$, dimethyl ether, $CO_2$ and air and antioxidants.

To produce the colorants according to the invention, the constituents of the water-containing carrier are used in the usual quantities for this purpose. For example, emulsifiers are used in concentrations of 0.5 to 30% by weight while thickeners are used in concentrations of 0.1 to 25% by weight, based on the colorant as a whole.

It can be of advantage to the coloring result to add ammonium or metal salts to the colorants. Suitable metal salts are, for example, formates, carbonates, halides, sulfates, butyrates, valerates, caproates, acetates, lactates, glycolates, tartrates, citrates, gluconates, propionates, phosphates and phosphonates of alkali metals, such as potassium, sodium or lithium, alkaline earth metals, such as magnesium, calcium, strontium or barium, or of aluminium, manganese, iron, cobalt, copper or zinc, sodium acetate, lithium bromide, calcium bromide, calcium gluconate, zinc chloride, zinc sulfate, magnesium chloride, magnesium sulfate, ammonium carbonate, chloride and acetate being preferred. These salts are preferably present in a quantity of 0.03 to 65 mmol and more preferably in a quantity of 1 to 40 mmol, based on 100 g of the colorant as a whole.

The pH value of the ready-to-use coloring compositions is normally in the range from 2 to 12 and preferably in the range from 4 to 10.

The present invention also relates to the use of a combination of heteroaromatic aldehydes and ketones corresponding to formula I:

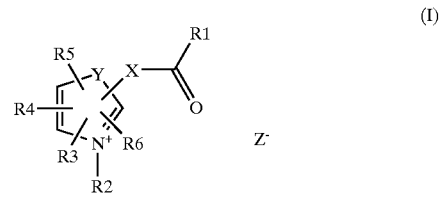

in which $R^1$ is a hydrogen atom, a $C_{1-4}$ alkyl group, an aryl or heteroaryl group, $R^2$ is a $C_{1-4}$ alkyl group, an aryl, aralkyl or heteroaryl group, $R^3$, $R^4$, $R^5$ and $R^6$ represent a hydrogen or halogen atom, a $C_{1-4}$ alkyl, $C_{1-4}$ alkoxy or $C_{1-4}$ hydroxyalkoxy group, a hydroxy, nitro or amino group, which may be substituted by $C_{1-4}$ alkyl groups, or a $C_{1-4}$ acyl group; two of the substituents together may also form a fused aromatic ring or one of the substituents together with with $R^1$ or with $R^2$ may form a fused 5-, 6- or 7-membered ring which may also carry a fused aromatic ring, X is a direct bond, an optionally substituted vinylene, phenylene or vinylenephenylene group, Y is a sulfur atom, an oxygen atom, the group $CR^7R^8$, where $R^7$ and $R^8$ represent a $C_{1-4}$ alkyl group, the group $NR^{10}$, where $R^{10}$ is a $C_{1-4}$ alkyl group, or an optionally substituted vinylene group and $Z^-$ is halide, $C_{1-4}$ alkyl sulfate, arene sulfate, $C_{1-4}$ alkanesulfonate, $C_{1-4}$ perfluoroalkane sulfonate, perhalogenate, sulfate, hydrogen sulfate, tetrafluoroborate, hexafluorophosphate or tetrachlorozincate, and aromatic or heteroaromatic nitroamines corresponding to formula II:

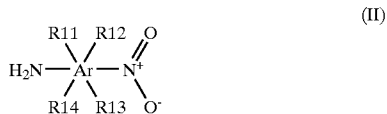

(II)

in which
- AR represents benzene, naphthalene, pyridine, quinoline, isoquinoline, pyrimidine, indole, benzimidazole, benzothiazole, indazole, benzoxazole, quinoxaline, quinazoline, cinnoline, acenaphthene, fluorene, biphenyl, diphenylmethane, benzophenone, azobenzene, azonaphthalene, 1-arylazonaphthalene, 2-arylazonaphthalene, diphenylamine, stilbene, benzylidene aminobenzene and
- $R^{11}$, $R^{12}$, $R^{13}$ and $R^{14}$ represent a hydrogen atom, a halogen atom, a $C_{1-4}$ alkyl, $C_{1-4}$ alkoxy, $C_{1-4}$ aminoalkyl, $C_{1-4}$ hydroxyalkoxy, hydroxy, nitro, carboxy, $C_{1-4}$ alkoxycarbonyl, sulfo, sulfamoyl, arylazo or amino group which may be substituted by $C_{1-4}$ alkyl or $C_{1-4}$ hydroxyalkyl groups,
- and/or a reaction product of the compounds corresponding to formulae I and II, as a coloring component in oxidation hair colorants.

The present invention also relates to a process for coloring keratin-containing fibers, more particularly human hair, in which a colorant containing a combination of heteroaromatic aldehydes and ketones corresponding to formula I:

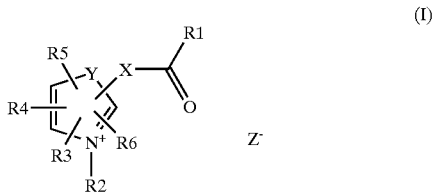

(I)

in which
- $R^1$ is a hydrogen atom, a $C_{1-4}$ alkyl group, an aryl or heteroaryl group,
- $R^2$ is a $C_{1-4}$ alkyl group, an aryl, aralkyl or heteroaryl group,
- $R^3$, $R^4$, $R^5$ and $R^6$ represent a hydrogen or halogen atom, a $C_{1-4}$ alkyl, $C_{1-4}$ alkoxy or $C_{1-4}$ hydroxyalkoxy group, a hydroxy, nitro or amino group, which may be substituted by $C_{1-4}$ alkyl groups, or a $C_{1-4}$ acyl group; two of the substituents together may also form a fused aromatic ring or one of the substituents together with with $R^1$ or with $R^2$ may form a fused 5-, 6- or 7-membered ring which may also carry a fused aromatic ring,
- X is a direct bond, an optionally substituted vinylene, phenylene or vinylenephenylene group,
- Y is a sulfur atom, an oxygen atom, the group $CR^7R^8$, where $R^7$ and $R^8$ represent a $C_{1-4}$ alkyl group, the group $NR^{10}$, where $R^{10}$ is a $C_{1-4}$ alkyl group, or an optionally substituted vinylene group and
- $Z^-$ is halide, $C_{1-4}$ alkyl sulfate, arene sulfate, $C_{1-4}$ alkanesulfonate, $C_{1-4}$ perfluoroalkane sulfonate, perhalogenate, sulfate, hydrogen sulfate, tetrafluoroborate, hexafluorophosphate or tetrachlorozincate, and aromatic or heteroaromatic nitroamines corresponding to formula II:

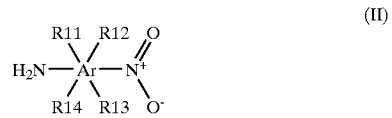

(II)

in which
- AR represents benzene, naphthalene, pyridine, quinoline, isoquinoline, pyrimidine, indole, benzimidazole, benzothiazole, indazole, benzoxazole, quinoxaline, quinazoline, cinnoline, acenaphthene, fluorene, biphenyl, diphenylmethane, benzophenone, azobenzene, azonaphthalene, 1-arylazonaphthalene, 2-arylazonaphthalene, diphenylamine, stilbene, benzylidene aminobenzene and
- $R^{11}$, $R^{12}$, $R^{13}$ and $R^{14}$ represent a hydrogen atom, a halogen atom, a $C_{1-4}$ alkyl, $C_{1-4}$ alkoxy, $C_{1-4}$ aminoalkyl, $C_{1-4}$ hydroxyalkoxy, hydroxy, nitro, carboxy, $C_{1-4}$ alkoxycarbonyl, sulfo, sulfamoyl, arylazo or amino group which may be substituted by $C_{1-4}$ alkyl or $C_{1-4}$ hydroxyalkyl groups,
- and/or a reaction product of these compounds and typical cosmetic ingredients is applied to the keratin-containing fibers, left thereon for a while, usually about 30 minutes, and then rinsed out or washed out with a shampoo.

The heteroaromatic aldehydes and ketones corresponding to formula I and the aromatic or heteroaromatic nitroamines corresponding to formula II may be applied to the hair either simultaneously or successively; in the latter case, it does not matter which of the two components is applied first. The ammonium or metal salts optionally present may be added to the first component or to the second component. A period of up to 30 minutes may elapse between application of the first component and the second component. The fibers may also be pretreated with the salt solution.

The heteroaromatic aldehydes and ketones corresponding to formula I and the aromatic or heteroaromatic nitroamines corresponding to formula II may be stored either separately or together either in a liquid or paste-form preparation (water-based or water-free) or as a dry powder. In the event of separate storage, the components are thoroughly mixed together just before application. In the event of dry storage, a certain quantity of warm (30 to 80° C.) water is normally added and a homogeneous mixture prepared before application.

EXAMPLES

Preparation of a Coloring Solution

Suspensions of 5.0 mmol of an aromatic aldehyde or ketone corresponding to formula I and 5.0 mmol of a nitroamine corresponding to formula II in 25 ml of water at 50° C. were prepared. After cooling to 30° C., the suspensions were mixed together, 5 mmol of sodium acetate and one drop of a 20% fatty alkyl ether sulfate solution were added and the pH (6.0 unless otherwise indicated) was adjusted accordingly with dilute NaOH or hydrochloric acid.

A tress of 90% grey, non-pretreated human hair was placed in this coloring solution for 30 minutes at 30° C. The tress was then rinsed for 30 seconds with luke-warm water, dried with warm air and then combed out.

The particular shades and depths of color are shown in the following Tables.

The depth of color was evaluated on the following scale:
-: very faint, if any, color
(+): weak intensity
+: medium intensity
+(+): medium to strong intensity
++: strong intensity
++(+): strong to very strong intensity
+++: very strong intensity

TABLE 1

| Aldehyde | Nitroamine | Color | Intensity |
|---|---|---|---|
| 4-Benzoyl-1-methylpyridinium methanesulfonate | 2-(2-Amino-4-nitroanilino)-ethanol (HC Yellow 5) | Bright orange | +++ |
| 4-Benzoyl-1-methylpyridinium methanesulfonate | 1-(2-hydroxyethylamino-2-nitro-4-aminobenzene (HC Red 3) | Violet-red | +++ |
| 4-Benzoyl-1-methylpyridinium methanesulfonate | 1-Amino-2-nitro-4-[bis-(2-hydroxyethyl)-amino]-benzene (HC Red 13, Cardinal Red) | Dark violet | +++ |
| 4-Benzoyl-1-methylpyridinium methanesulfonate | 4-Amino-3-nitrophenol | Neutral red | +++ |
| 4-Benzoyl-1-methylpyridinium methanesulfonate | 2-Nitro-3-amino-6-aminomethylpyridine (Aza Red) | Orange | ++ |
| 4-Benzoyl-1-methylpyridinium methanesulfonate | Basic Brown 17 | Orange-brown | ++ |
| 4-Formyl-1-methylquinolinium-p-toluenesulfonate | 2-(2-Amino-4-nitroanilino)-ethanol (HC Yellow 5) | Violet-black | +++ |
| 4-Formyl-1-methylquinolinium-p-toluenesulfonate | 2-Nitro-3-amino-6-aminomethyl pyridine (Aza Red) | Brown-pink | +(+) |
| 4-Formyl-1-methylquinolinium-p-toluenesulfonate | 1-(2-Hydroxyethylamino)-2-nitro-4-aminobenzene (HC Red) | Dark red | +++ |
| 4-Formyl-1-methylquinolinium-p-toluenesulfonate | 1-Amino-2-nitro-4-[bis-(2-hydroxyethyl)-amino]-benzene (HC Red 13, Cardinal Red) | Blue-violet | +++ |
| 4-Formyl-1-methylpyridinium benzenesulfonate | 2-(2-Amino-4-nitroanilino)-ethanol (HC Yellow 5) | Neutral red | ++(+) |
| 4-Formyl-1-methylpyridinium benzenesulfonate | 2-(4-Amino-2-nitroanilino)-benzoic acid | Orange-brown | + |
| 4-Formyl-1-methylpyridinium benzenesulfonate | 2-Amino-4-nitro-6-chlorophenol (Rodol 9R Base) | Brown-orange | + |
| 4-Formyl-1-methylpyridinium benzenesulfonate | 1-Amino-2-nitro-4-[bis-(2-hydroxyethyl)-amino]-benzene (HC Red 13, Cardinal Red) | Blue-violet | +++ |
| 4-Formyl-1-methylquinolinium-p-toluenesulfonate | 2-Amino-nitrobenzothiazole* | Orange-brown | ++ |
| 4-Formyl-1-methylpyridinium benzenesulfonate | 4-Amino-3-nitrophenol | Bright red | ++(+) |
| 4-Formyl-1-methylpyridinium benzenesulfonate | 2-Nitro-p-phenylenediamine | Violet-red | ++(+) |
| 4-Formyl-1-methylpyridinium benzenesulfonate | Picramic acid | Neutral red | ++ |
| 4-Formyl-1-methylpyridinium benzenesulfonate | 2-Amino-6-nitrobenzothiazole* | Light brown | + |
| 2-Formyl-1-methylquinolinium-p-toluenesulfonate | 2-Amino-4-nitro-6-chlorophenol (Rodol 9 R Base)* | Brown-orange | ++(+) |
| 4-Formyl-1-methylquinolinium-p-toluenesulfonate | 1-Amino-2-nitro-4-[bis-(2-hydroxyethyl)-amino[-benzene (HC Red 13, Cardinal Red) | Violet-blue-black | +++ |
| 2-Formyl-1-methylquinolinium-p-toluenesulfonate | 1-Amino-2-nitro-4-[bis-(2-hydroxyethyl)-amino]-benzene (HC Red No. 13, Cardinal Red) | Violet-black | +++ |
| 2-Formyl-1-methylquinolinium-p-toluenesulfonate | 2-(2-Amino-4-nitroanilino)-ethanol (HC Yellow 5) | Yellow-brown | ++ |
| 2-Formyl-1-methylquinolinium-p-toluenesulfonate | 1-(2-Hydroxyethylamino)-2-nitro-4-aminobenzene (HC Red 3) | Violet-brown | ++(+) |
| 2-Formyl-1-methylquinolinium-p-toluenesulfonate | 4-Amino-3-nitrophenol | Orange-brown | ++ |

*with an equimolar quantity of piperidine as color intensifier at pH = 9

What is claimed is:
1. A composition for coloring keratin-containing fibers comprising a mixture of, or a reaction product of, or both of:
(A) at least one heteroaromatic aldehyde or ketone corresponding to formula I:

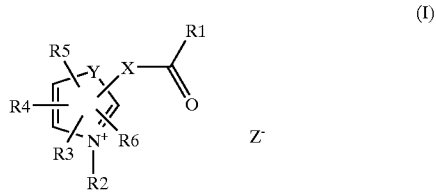

wherein $R^1$ is a hydrogen atom, a $C_{1-4}$ alkyl group, or an aryl or heteroaryl group, wherein $R^2$ is a $C_{1-4}$ alkyl group, or an aryl, aralkyl or heteroaryl group, wherein $R^3$, $R^4$, $R^5$ and $R^6$, independently of one another, represent a hydrogen atom, a halogen atom, a $C_{1-4}$ alkyl group, a $C_{1-4}$ alkoxy group, a $C_{1-4}$ hydroxyalkoxy group, a hydroxy group, a nitro group or an amino group in which the amino group may optionally be substituted by at least one $C_{1-4}$ alkyl group, or $C_{1-4}$ acyl group, or wherein at least two of $R^3$, $R^4$, $R^5$ or $R^6$ may form together a fused aromatic ring, or wherein at least one of $R^3$, $R^4$, $R^5$ or $R^6$ together with $R^1$ or $R^2$ may form a fused 5-, 6- or 7-membered ring in which the fused 5-, 6- or 7-membered ring may optionally have attached thereto another fused aromatic ring, wherein X is a direct bond, or a substituted or unsubstituted vinylene, phenylene or vinylenephenylene group, wherein Y is a sulfur atom, an oxygen atom, a $CR^7R^8$ group, an $NR^{10}$ group, or a substituted or unsubstituted vinylene group in which $R^7$, $R^8$ and $R^{10}$, independently of one another, represent a $C_{1-4}$ alkyl group, and wherein $Z^-$ is a halide, a $C_{1-4}$ alkyl sulfate, an arene sulfate, a $C_{1-4}$ alkanesulfonate, a $C_{1-4}$ perfluoroalkane sulfonate, a perhalogenate, a sulfate, hydrogen sulfate, tetrafluoroborate, hexafluorophosphate or tetrachlorozincate; and (B) at least one heteroaromatic nitroamine corresponding to formula II:

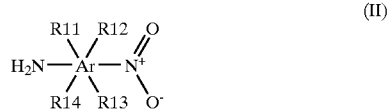

wherein AR represents pyridine, quinoline, isoquinoline, pyrimidine, indole, benzimidazole, benzothiazole, indazole, benzoxazole, quinoxaline, quinazoline, or cinnoline, and $R^{11}$, $R^{12}$, $R^{13}$ and $R^{14}$, independently of one another, represent a hydrogen atom, a halogen atom, a $C_{1-4}$ alkyl group, a $C_{1-4}$ alkoxy group, a $C_{1-4}$ aminoalkyl group, a $C_{1-4}$ hydroxyalkoxy group, a hydroxy group, a nitro group, a carboxy group, a $C_{1-4}$ alkoxycarbonyl group, a sulfo group, a sulfamoyl group, an arylazo group or an amino group in which the amino group may optionally be substituted by a $C_{1-4}$ alkyl group or a $C_{1-4}$ hydroxyalkyl group.

2. The composition of claim 1 wherein the heteroaromatic aldehyde or ketone of formula I comprises a salt of a compound selected from 4-formyl-1-methylpyridinium, 2-formyl-1-methylpyridinium, 4-formyl-1-ethylpyridinium, 2-formyl-1-ethylpyridinium, 4-formyl-1-benzylpyridinium, 2-formyl-1-benzylpyridinium, 4-formyl-1,2-dimethylpyridinium, 4-formyl-1,3-dimethylpyridinium, 4-formyl-1-methylquinolinium, 2-formyl-1-methylquinolinium, 5-formyl-1-methylquinolinium, 6-formyl-1-methylquinolinium, 7-formyl-1-methylquinolinium, 8-formyl-1-methylquinolinium, 4-acetyl-1-methylpyridinium, 2-acetyl-1-methylpyridinium, 4-acetyl-1-methylquinolinium, 5-acetyl-1-methylquinolinium, 6-acetyl-1-methylquinolinium, 7-acetyl-1-methylquinolinium, 8-acetyl-1-methylquinolinium, 9-formyl-10-methylacridinium, 4-(2-formylvinyl)-1-methylpyridinium, 1,3-dimethyl-2-(4-formylphenyl)-benzimidazolinium, 1,3-dimethyl-2-(4-formylphenyl)-imidazolinium, 2-(4-formylphenyl)-3-methylbenzothiazolium, 2-(4-acetylphenyl)-3-methylbenzothiazolium, 2-(4-formylphenyl)-3-methylbenzoxazolium, 2-(5-formyl-2-furyl)-3-methylbenzothiazolium, 2-(5-formyl-2-furyl)-3-methylbenzothiazolium, 2-(5-formyl-2-thienyl)-3-methylbenzothiazolium, 2-(3-formylphenyl)-3-methylbenzothiazolium, 2-(4-formyl-1-naphthyl)-3-methylbenzothiazolium, 5-chloro-2-(4-formylphenyl)-3-methylbenzothiazolium, 2-(4-formylphenyl)-3,5-dimethylbenzothiazolium, 1-methyl-2-[2-(4-formylphenyl)-ethenyl]-pyridinium, 1-methyl-4-[2-(4-acetylphenyl)-ethenyl]-pyridinium, 1-benzyl-4-[2-(4-formylphenyl)-ethenyl]-pyridinium, 1-methyl-4-[2-(4-formylphenyl)-ethenyl]-pyridinium, 1-methyl-2-[2-(4-formylphenyl)-ethenyl]-pyridinium, 1-methyl-4-[2-(4-formylphenyl)-ethenyl]-quinolinium, 1-methyl-2-[2-(4-formylphenyl)-ethenyl]-quinolinium, 1-methyl-2-[2-(5-formyl-2-furyl)-ethenyl]-quinolinium, 1-methyl-2-[2-(5-formyl-2-thienyl)-ethenyl]-quinolinium, 1-methyl-2-[2-(4-formylphenyl) ethenyl]-benzothiazolinium, 1,3-dimethyl-2-[2-(4-formylphenyl)-ethenyl]-benzimidazolinium, 1,3-dimethyl-2-[2-(4-formylphenyl)-ethenyl]-imidazolinium, 1-methyl-5-oxo-indeno[1,2-b]pyridinium, 1-ethyl-5-oxo-indeno[1,2-b]pyridinium, 1-benzyl-5-oxo-indeno[1,2-b]pyridinium, 2-methyl-5-oxo-indeno[1,2-c]pyridinium, 2-methyl-9-oxo-indeno[2,1-c]pyridinium or 1-methyl-9-oxo-indeno[2,1-b]pyridinium, or mixtures thereof.

3. The composition of claim 2 wherein $Z^-$ of the salt is selected from one or more benzenesulfonates, p-toluenesulfonates, methansulfonates, perchlorates, sulfates, chlorides, bromides, iodides, tetrachlorozincates, methyl sulfates, trifluoromethanesulfonates, hexafluorophosphates, tetrafluroborates or mixtures thereof.

4. The composition of claim 1, wherein the heteroaromatic nitroamine is selected from 3-amino-6-methylamino-2-nitropyridine, or 6-nitro-2,5-diaminopyridine or mixtures thereof.

5. The composition of claim 1 wherein the heteroaromatic aldehyde or ketone and the heteroaromatic nitroamine are each used in quantities of 0.03 mmol to 65 mmol, based on 100 grams of the composition as a whole.

6. The composition of claim 5 wherein the heteroaromatic aldehyde or ketone and the heteroaromatic nitroamine are each used in quantities of 1 mmol to 40 mmol, based on 100 grams of the composition as a whole.

7. The composition of claim 1, further comprising one or more color intensifiers selected from piperidine, piperidine-2-carboxylic acid, piperidine-3-carboxylic acid, piperidine- 4-carboxylic acid, pyridine, 2-hydroxypyridine, 3-hydroxypyridine, 4-hydroxypyridine, imidazole, 1-methyl imidazole, histidine, pyrrolidine, proline, pyrrolidone, pyrrolidone-5-carboxylic acid, pyrazole, 1,2,4-triazole or piperazidine, or mixtures thereof.

8. The composition of claim 1 further comprising from 0.01 weight percent to 20 weight percent, based on the total weight of the composition, of one or more substantive dyes selected from nitrophenylenediamines, nitroaminophenols, anthraquinones or indophenols, or combinations thereof.

9. The composition of claim 1 further comprising one or more ammonium or metal salts selected from formates, carbonates, halides, sulfates, butyrates, valerates, caproates, acetates, lactates, glycolates, tartrates, citrates, gluconates, propionates, phosphates or phosphonates or combinations thereof.

10. The composition of claim 9 wherein the cationic component of the ammonium or metal salts comprises one or more ammonium ions, alkali metals, alkaline earth metals, aluminum, manganese, iron, cobalt, copper or zinc or mixtures thereof.

11. The composition of claim 1 further comprising one or more oxidizing agents.

12. The composition of claim 1 wherein the oxidizing agents comprise from 0.01 weight percent to 6 weight percent $H_2O_2$, based on the total weight of the composition.

13. The composition of claim 1, further comprising one or more anionic, zwitterionic or nonionic surfactants, or combinations thereof.

14. A process for coloring keratin-containing fibers comprising applying to keratin containing fibers
   (a) at least one heteroaromatic aldehyde or ketone corresponding to formula I:

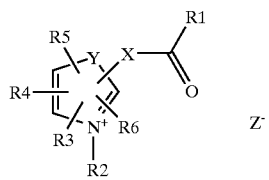

(I)

wherein $R^1$ is a hydrogen atom, a $C_{1-4}$ alkyl group, or an aryl or heteroaryl group,
wherein $R^2$ is a $C_{1-4}$ alkyl group, or an aryl, aralkyl or heteroaryl group,
wherein $R^3$, $R^4$, $R^5$ and $R^6$, independently of one another, represent a hydrogen atom, a halogen atom, a $C_{1-4}$ alkyl group, a $C_{1-4}$ alkoxy group, a $C_{1-4}$ hydroxyalkoxy group, a hydroxy group, a nitro group or an amino group in which the amino group may optionally be substituted by at least one $C_{1-4}$ alkyl group, or $C_{1-4}$ acyl group, or wherein at least two of $R^3$, $R^4$, $R^5$ or $R^6$ may form together a fused aromatic ring, or wherein at least one of $R^3$, $R^4$, $R^5$ or $R^6$ together with $R^1$ or $R^2$ may form a fused 5-, 6- or 7-membered ring in which the fused 5-, 6- or 7-membered ring may optionally have attached thereto another fused aromatic ring,
wherein X is a direct bond, or a substituted or unsubstituted vinylene, phenylene or vinylenephenylene group,
wherein Y is a sulfur atom, an oxygen atom, a $CR^7R^8$ group, an $NR^{10}$ group, or a substituted or unsubstituted vinylene group in which $R^7$, $R^8$ and $R^{10}$, independently of one another, represent a $C_{1-4}$ alkyl group, and
wherein $Z^-$ is a halide, a $C_{1-4}$ alkyl sulfate, an arene sulfate, a $C_{1-4}$ alkanesulfonate, a $C_{1-4}$ perfluoroalkane sulfonate, a perhalogenate, a sulfate, hydrogen sulfate, tetrafluoroborate, hexafluorophosphate or tetrachlorozincate; and (b) at least one heteroaromatic nitroamine corresponding to formula II:

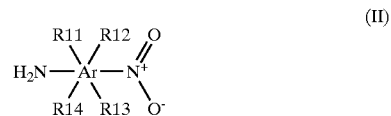

(II)

wherein AR represents pyridine, quinoline, isoquinoline, pyrimidine, indole, benzimidazole, benzothiazole, indazole, benzoxazole, quinoxaline, quinazoline, or cinnoline, and $R^{11}$, $R^{12}$, $R^{13}$ and $R^{14}$, independently of one another, represent a hydrogen atom, a halogen atom, a $C_{1-4}$ alkyl group, a $C_{1-4}$ alkoxy group, a $C_{1-4}$ aminoalkyl group, a $C_{1-4}$ hydroxyalkoxy group, a hydroxy group, a nitro group, a carboxy group, a $C_{1-4}$ alkoxycarbonyl group, a sulfo group, a sulfamoyl group, an arylazo group or an amino group in which the amino group may optionally be substituted by a $C_{1-4}$ alkyl group or a $C_{1-4}$ hydroxyalkyl group.

15. The method of claim 14 wherein the heteroaromatic aldehyde or ketone and the heteroaromatic nitroamine are applied simultaneously or successively in any order to the keratin-containing fibers.

16. The method of claim 14 wherein the heteroaromatic aldehyde or ketone and the heteroaromatic nitroamine are formulated into a coloring composition prior to the applying step.

17. The method of claim 16 wherein the coloring composition comprises a reaction product of the heteroaromatic aldehyde or ketone and the heteroaromatic nitroamine.

18. The method of claim 14 wherein the keratin-containing fiber is hair and following the applying step, the heteroaromatic aldehyde or ketone and the heteroaromatic nitroamine are washed out with a shampoo or rinsed out from the hair after a contact time of about 30 minutes.

* * * * *

UNITED STATES PATENT AND TRADEMARK OFFICE
CERTIFICATE OF CORRECTION

PATENT NO. : 6,755,872 B1
DATED : June 29, 2004
INVENTOR(S) : Moeller et al.

It is certified that error appears in the above-identified patent and that said Letters Patent is hereby corrected as shown below:

<u>Title page</u>,
Item [75], Inventors, delete "Monhelm" and insert -- Monheim --.

<u>Column 17</u>,
Line 24, delete "claim 1" and insert -- claim 11 --.

Signed and Sealed this

Sixteenth Day of November, 2004

JON W. DUDAS
*Director of the United States Patent and Trademark Office*